(12) United States Patent
Ewer

(10) Patent No.: US 10,857,549 B2
(45) Date of Patent: Dec. 8, 2020

(54) METHODS AND APPARATUS FOR SEPARATING FLUID COMPONENTS

(71) Applicant: Royal Biologics, Jersey City, NJ (US)

(72) Inventor: Darin Ewer, Providence, UT (US)

(73) Assignee: Royal Biologics, Jersey City, NJ (US)

( * ) Notice: Subject to any disclaimer, the term of this patent is extended or adjusted under 35 U.S.C. 154(b) by 0 days.

(21) Appl. No.: 16/355,636

(22) Filed: Mar. 15, 2019

(65) Prior Publication Data

US 2019/0210040 A1     Jul. 11, 2019

Related U.S. Application Data

(62) Division of application No. 15/358,606, filed on Nov. 22, 2016, now Pat. No. 10,272,445.

(60) Provisional application No. 62/259,413, filed on Nov. 24, 2015.

(51) Int. Cl.
| | |
|---|---|
| *B04B 5/04* | (2006.01) |
| *A61M 1/02* | (2006.01) |
| *A61M 1/36* | (2006.01) |
| *B01L 3/00* | (2006.01) |
| *A61K 35/16* | (2015.01) |
| *A61K 35/19* | (2015.01) |
| *A61J 1/20* | (2006.01) |

(52) U.S. Cl.
CPC ............ *B04B 5/0414* (2013.01); *A61K 35/16* (2013.01); *A61K 35/19* (2013.01); *A61M 1/02* (2013.01); *A61M 1/3693* (2013.01); *B01L 3/5021* (2013.01); *A61J 1/2096* (2013.01)

(58) Field of Classification Search
CPC ...... B04B 5/0414; A61K 35/16; A61K 35/19; A61J 1/2096; B01L 3/5021
See application file for complete search history.

(56) References Cited

U.S. PATENT DOCUMENTS 7,179,391 B2 *    2/2007    Leach ................. B01D 17/0217
                                                                           210/782

* cited by examiner

*Primary Examiner* — Timothy C Cleveland
(74) *Attorney, Agent, or Firm* — David Meibos; Maywood IP Law

(57) ABSTRACT

An apparatus and method may be used to separate a biological liquid sample and retrieve a separated liquid portion therefrom. The apparatus may have a tube, an insert, and a positioning mechanism. The tube may have a proximal end, a distal end, and a chamber between the proximal and distal ends for receiving the biological liquid sample. The insert may be positioned in the chamber, and may have a first end, a second end, a well between the first and second ends, and a draw tube in fluid communication with the second end and the well. The positioning mechanism may be connected to the tube and the insert, and may be manually actuable to move the insert between the proximal end and distal end to allow a separated portion of the biological liquid sample to flow proximally from the chamber through the draw tube and collect in the well.

20 Claims, 9 Drawing Sheets

METHODS AND APPARATUS FOR SEPARATING FLUID COMPONENTS

CROSS-REFERENCE TO RELATED APPLICATIONS

This application is a divisional application of U.S. patent application Ser. No. 15/358,606, filed Nov. 22, 2016, entitled METHODS AND APPARATUS FOR SEPARATING FLUID COMPONENTS, which claims the benefit of U.S. Provisional Application Ser. No. 62/259,413, filed Nov. 24, 2015, entitled METHODS AND APPARATUS FOR SEPARATING FLUID COMPONENTS. The foregoing are incorporated by reference as though set forth herein in their entirety.

TECHNICAL FIELD

The present invention relates to devices and methods for separating biological fluids into component products. More specifically, the present invention relates to apparatus and methods for concentrating platelet-rich plasma for use in surgical and medical procedures.

BACKGROUND

Platelet-rich blood plasma is required for use in various medical procedures. This blood product is particularly effective due to its growth promoting features, which assist greatly in wound healing and bone regeneration. Blood plasma with a high concentration of platelets can be utilized for dental implants and other periodontal procedures, facial reconstruction, oral or maxillofacial surgery, and chronic wound care, among other uses. In order to obtain a required concentration of platelets, a blood sample is usually centrifuged in order to separate the blood into its component blood products (i.e. plasma, red blood cells and platelets). The platelets, typically in a form of a white "buffy coat," are then separated from the blood sample and sequestered in concentrated form through aspiration. Conventional aspiration techniques often fail to provide a satisfactory concentration of platelets.

SUMMARY OF THE INVENTION

The various systems and methods of the present invention have been developed in response to the present state of the art, and in particular, in response to the problems and needs in the art that have not yet been fully solved by currently available aspiration systems and methods. The systems and methods of the present invention may provide efficient and effective concentration and retrieval of separated blood products. The devices and methods disclosed herein may be used to separate any suitable fluid; for example blood or bone marrow aspirate (BMA), among others.

To achieve the foregoing, and in accordance with the invention as embodied and broadly described herein, various systems and methods are disclosed herein, for separating a sample of liquid such as blood contained in a chamber. Such systems and methods may be used to order the phases or fractions of a sample of liquid contained in a chamber by applying a force to the fluid. In particular, an apparatus according to the present disclosure may have a tubular chamber in which a blood sample can be received. Centrifugal force may be applied to the tubular chamber to separate the phases of the blood sample. The one or more separated phases may then be removed from the chamber.

Specifically, the chamber may be a fluid sample tube having ends separated by a dividing insert. A first end of the tube may receive a sample of fluid. The tube may then be rotated (for example, in a centrifuge) to separate the phases. The dividing insert may be selectively positioned to capture a pre-selected phase of the fluid. The pre-selected phase of the fluid may be received from the first end of the tube. The systems and methods disclosed herein may be used to separate any suitable fluid; for example blood or bone marrow aspirate (BMA), among others.

In one embodiment, an apparatus for separating a biological liquid sample and retrieve a separated liquid portion therefrom may have a tube, an insert, and a positioning mechanism. The tube may have a proximal end, a distal end, and a chamber between the proximal end and the distal end for receiving the biological liquid sample. The insert may be positioned in the chamber, and may have a first end, a second end, a well between the first end and the second end, and a draw tube in fluid communication with the second end and the well. The positioning mechanism may be connected to the tube and the insert, and may be manually actuable to move the insert between the proximal end and distal end to allow a separated portion of the biological liquid sample to flow proximally from the chamber through the draw tube and collect in the well.

The positioning mechanism may define a longitudinal axis, and the insert may be translatable relative to the tube and the positioning mechanism along the longitudinal axis. The positioning mechanism may be a lead screw extending from the proximal end into the chamber toward the distal end. The lead screw may pass through the insert. The insert may be movable along a continuum extending from the proximal end toward the distal end, and may be positioned at any selected location along the continuum. The apparatus may further have a lid enclosing the proximal end; the lid may include a first port and a second port displaced from the first port, each port providing selective access into the chamber. The insert may be positioned at the proximal end. The first port may be directly connected to the draw tube to allow the biological liquid sample to be deposited distally through the first port, through the draw tube and into the chamber distal to the insert. When the insert may be distally displaced from the proximal end, the first port may be disconnected from the draw tube.

The apparatus may further have an O-ring positioned between the insert and the tube to prevent fluid movement between an outer surface of the insert and an inner surface of the chamber. The second end of the insert may be a radially asymmetrical concave distal face. The first end of the insert may be open, and the well may be open toward the proximal end.

In one embodiment, a method for separating a biological liquid sample and retrieve a separated liquid portion therefrom may include depositing the biological liquid sample into an apparatus including a tube with a proximal end, a distal end, and a chamber between the proximal end and the distal end, and an insert positioned in the chamber, with a first end, a second end, a well between the first end and the second end, and a draw tube in fluid communication with the second end and the well. Depositing the biological liquid sample into the apparatus may include depositing the biological liquid sample into the chamber, distal to the second end. The method may further include centrifuging the tube so that separated liquid collects in the chamber, distal to the second end, actuating a positioning mechanism connected to the tube and the insert, thereby moving the insert distally toward the separated liquid to allow the separated liquid to flow proximally from the chamber through the draw tube and collect in the well, and retrieving the separated liquid from the well.

The positioning mechanism may define a longitudinal axis. Moving the insert may include translating the insert relative to the tube and the positioning mechanism along the longitudinal axis. Further, the positioning mechanism may include a lead screw extending from the proximal end into the chamber toward the distal end. Actuating the positioning mechanism may include turning the lead screw. Moving the insert distally may include translating the insert from a first position at the proximal end toward the distal end, and stopping the insert at a selected position displaced distally from the proximal end.

Retrieving the separated liquid may include actuating the positioning mechanism, thereby moving the insert proximally toward the proximal end, and aspirating the separated liquid from the well. A lid may enclose the proximal end. The lid may include a first port and a second port displaced from the first port. Depositing the biological liquid sample into the chamber may include depositing the biological liquid sample through the first port, through the draw tube and into the chamber distal to the insert. Aspirating the separated liquid from the well may include aspirating the separated liquid from the well through the second port.

The method may further include centrifuging the biological liquid sample a second time. Further, the method may include centrifuging the biological liquid sample a third time, and actuating the positioning mechanism, thereby moving the insert distally toward the separated liquid to allow the separated liquid to flow proximally from the chamber through the draw tube and collect in the well.

Upon centrifugation of the tube, the biological liquid sample may separate into a first layer, a second layer, and an interface layer between the first and second layers. Retrieving the separated liquid may include retrieving the interface layer. The insert may remain stationary relative to the tube during centrifugation.

In one embodiment, a method for separating a biological liquid sample and retrieve a separated liquid portion therefrom may include depositing the biological liquid sample into an apparatus including a tube with a proximal end, a distal end, and a chamber between the proximal end and the distal end, and an insert positioned in the chamber, with a first end, a second end, a well between the first end and the second end. The method may further include centrifuging the tube a first time to separate the biological liquid sample into a first layer, a second layer, and an interface layer between the first and second layers, actuating a positioning mechanism to move the insert toward the interface layer and the distal end, and collecting the interface layer in the well. The method may further include, after actuating the positioning mechanism, centrifuging the tube a second time; after centrifuging the tube the second time, moving the insert toward the proximal end, and after moving the insert toward the proximal end, aspirating the interface layer from the well.

The method may further include, after centrifuging the tube the second time, actuating the positioning mechanism to move the insert toward the interface layer and the distal end a second time. Further, the method may include, after moving the insert toward the interface layer and the distal end the second time, collecting the interface layer in the well a second time. Yet further, the method may include, after collecting the interface layer in the well the second time, centrifuging the tube a third time.

These and other features and advantages of the present invention will become more fully apparent from the following description and appended claims, or may be learned by the practice of the invention as set forth hereinafter.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

DETAILED DESCRIPTION

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, system, and method, as represented in FIGS. 1A through 9, is not intended to limit the scope of the invention, as claimed, but is merely representative exemplary of exemplary embodiments of the invention.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figures 1A, 1B:
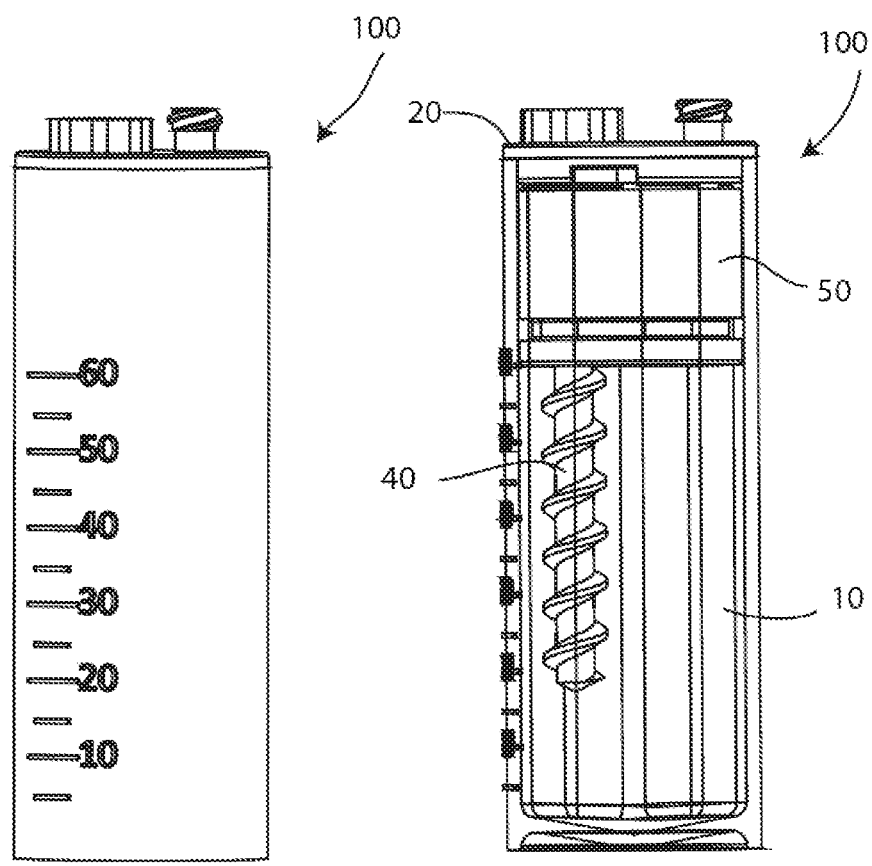
FIG. 1A is an front view of a fluid separation device comprising a tube having proximal and distal ends, a dividing insert, a positioning mechanism, and a lid on the tube proximal end.
FIG. 1B is a side transparent view of the device of FIG. 1A.
Figure 2:
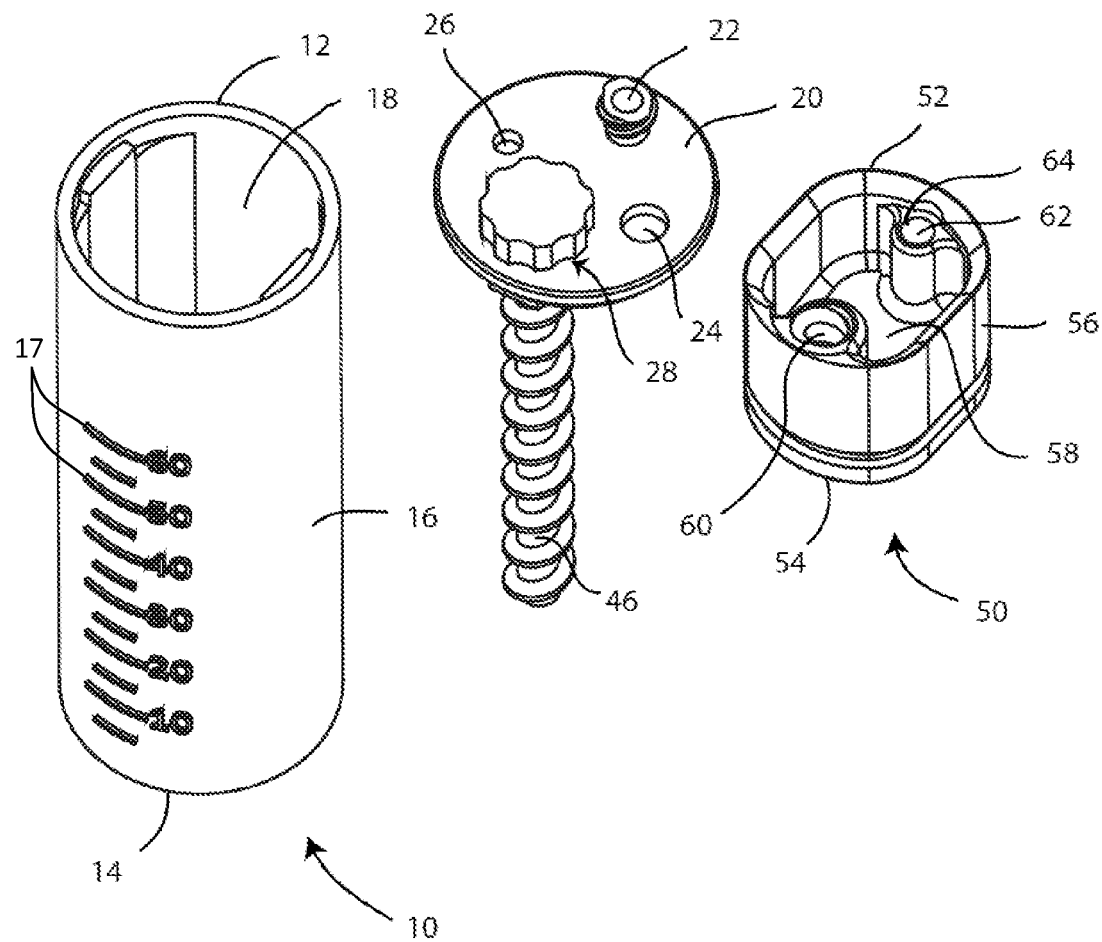
FIG. 2 is a partially exploded isometric view of the device of FIG. 1A from a top down perspective.

Referring to FIGS. 1A, 1B, and 2, an embodiment of a fluid separation device, or device 100, is shown. The device 100 includes a sample tube, or tube 10, a lid 20, a positioning mechanism 40, and an insert 50. The tube 10 may include a proximal or first end 12 which may be open, and a distal or second end 14 which may be blind or closed. A peripheral wall 16 encloses the tube longitudinally. Indicator marks 17 may be present on tube 10. A tube chamber 18 is bounded by the first end 12, second end 14, and peripheral wall 16. The tube chamber 18 may have a proximal end proximate the first end 12 of the tube 10, and distal end proximate the second end 14 of the tube 10.

The tube 10 and the insert 50 may be formed of any material suitable for maintaining a seal around a fluid. In some examples, the tube 10 and the insert 50 may be formed of a polymer, glass, or other material. Rigid (substantially non-deformable) materials may advantageously be used to help maintain seals and facilitate motion of the insert 50 within the tube 10. Further, the insert 50 need not be buoyant, as it is not designed to move relative to the tube 10 during the centrifugation process. Rather, the insert 50 may only be designed to move in response to user actuation of the positioning mechanism 40.

The exterior of tube 10 may be generally cylindrical. However, as can be seen in FIG. 2, the interior of tube 10 may be non-circular in cross section. The interior boundary shape of tube 10 may be complimentarily shaped relative to the exterior of insert 50. In the embodiment depicted, the interior of tube 10 and exterior of insert 50 are generally oval or D-shaped, and this may prevent rotation of insert 50 within tube 10 during motion of the insert 50 within the tube 10.

The lid 20 may include four openings: first port 22 which may be a fill or inlet port, second port 24 which may be an aspiration port, vent 26, and aperture 28, which may receive the positioning mechanism 40. The lid 20 may be removable, or may be permanently joined to the tube 10. Either or both of the first and second ports 22, 24 may be self-sealable or may comprise a plug. In some embodiments, either or both of the first and second ports 22, 24 may 0, be sealed through the use of a check valve or other structure permitting fluid to flow in only one direction. Vent 26 may be left open or may be covered and/or plugged. Other embodiments may include more or fewer openings. When properly assembled with tube 10, first port 22 extend through a boss 30 (shown in FIG. 3) that extends longitudinally into tube 10.

In the embodiment depicted, the positioning mechanism 40 comprises a lead screw 42. When properly assembled with the tube 10, lead screw 42 extends from the second end 14 through the tube chamber 18 toward the second end 14. In the embodiment shown, lead screw 42 is solid; i.e., it is not cannulated. Other embodiments of the invention may include a cannulated screw or other positioning mechanism.

Lead screw 42 includes a head 44 and threads 46. A nut 48 may secure lead screw 42 in aperture 28. Rotation of lead screw 42 about a longitudinal axis 49 in one direction urges insert 50 within tube 10 toward the distal end, i.e., the second end 14; rotation of lead screw 42 in the opposite direction urges insert 50 within tube 10 toward the proximal end, i.e., the first end 12. Thus, the insert 50 may translate relative to the tube 10 and relative to the lead screw, which may remain substantially stationary relative to the tube 10 and the insert 50, aside from the rotation of the lead screw 42 described above.

The lead screw 42 may also include indicia, markings, notches and/or other means to provide visual and/or tactile indication of the position of insert 50 within the tube 10. Additionally or alternatively, the peripheral wall 16 may be translucent so as to enable a user to visualize the position of the insert 50 within the tube chamber 18.

Figure 3:
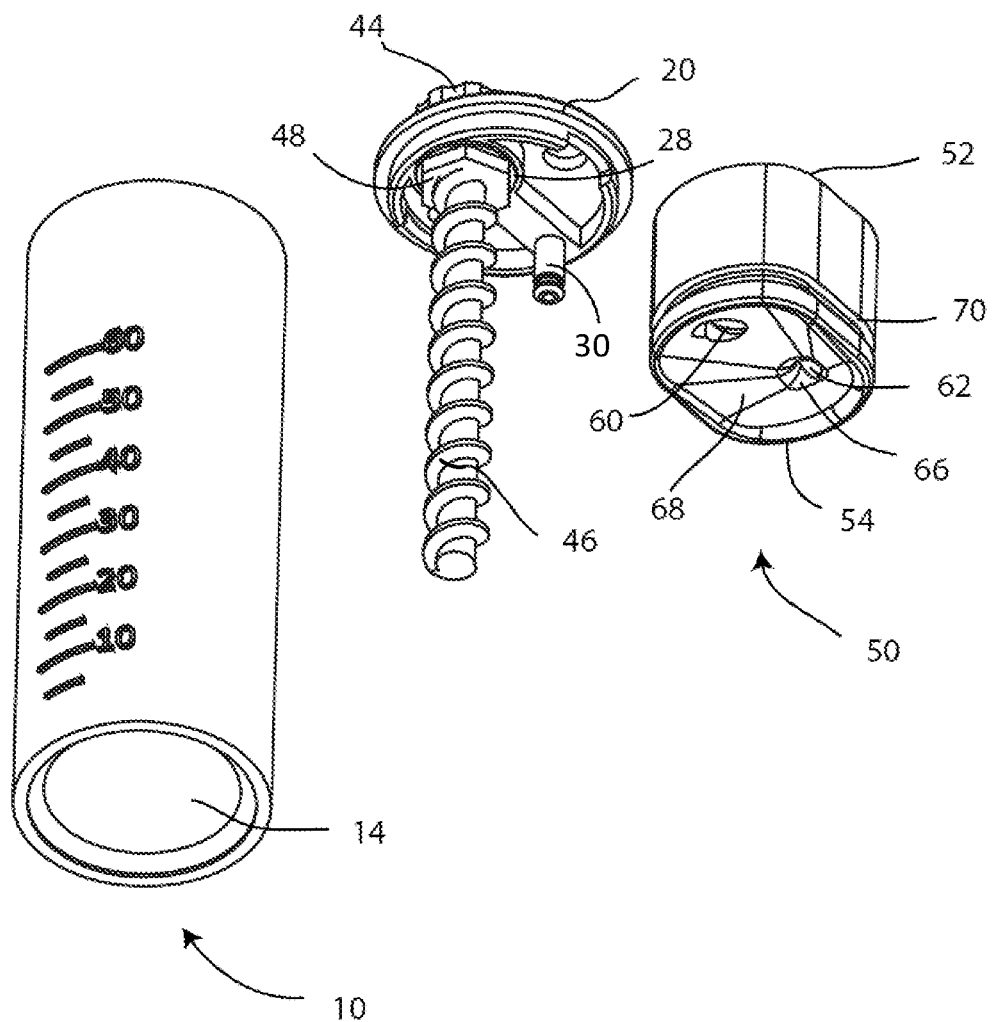
FIG. 3 is a partially exploded isometric view of the device of FIG. 1A from a bottom up perspective.
Figure 4:
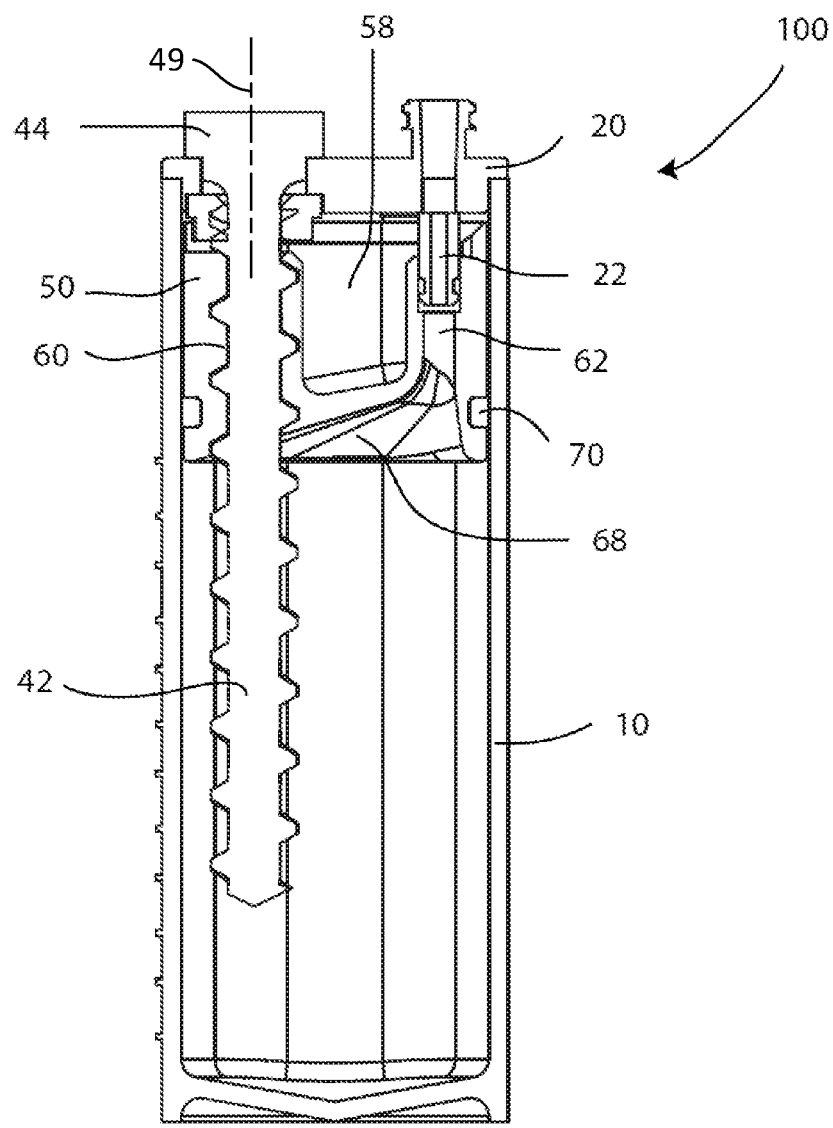
FIG. 4 is a side cross-sectional view of the device of FIG. 1A with the dividing insert in a proximal position wherein a draw tube of the insert is in communication with a first port of the lid.

Referring to FIGS. 2-4, insert 50 includes a first end 52 which may be an open end, a second end 54, and a peripheral wall 56 extending from the first end 52 to the second end 54. The insert 50 may also be referred to as a divider, or as a piston. A well 58 occupies the interior of the insert 50. A passageway 60 passes longitudinally through the insert 50. In the example shown passageway 60 is threaded to engage with threads 46 on the lead screw 42. In the example shown, passageway 60 is adjacent to the peripheral wall 56 and isolated from well 58. A draw tube 62 extends longitudinally along the insert 50. A first opening 64 of the draw tube 62 may be recessed from the first end 52 of the insert 50. A second opening 66 of the draw tube 62 opens out on the second end 54 of the insert 50. The second end 54 of the insert 50 may comprise a distal face 68, which is concave and may urge fluid flow toward the second opening of the draw tube 62. In the example shown, the distal face 68 is radially asymmetrical and non-conical. The insert 50 may further include a groove 70, which can house an O-ring 72 (shown in FIG. 5). Insert 50 may also be translucent so that the levels of fluids in the draw tube and the well 58 can be observed.

In one method of use, the device 100 is used with a centrifuge to separate and isolate a phase of a liquid, such as blood. Any of a wide variety of centrifuge types may be used; according to on example, the device 100 may be used with the @ Centrifuge, available from Eppendorf Belgium N.V.-S.A. The method may be used to separate, concentrate and collect the buffy coat layer which forms between red blood cells (RBC) and plasma layers during centrifugation. In additional, platelet rich plasma (PRP) may also be collected. The device 100 may be provided in a sterile package with the insert 50 pre-positioned at the top, i.e., proximate the first end 12 of the device so that it is ready to fill.

Figure 5:
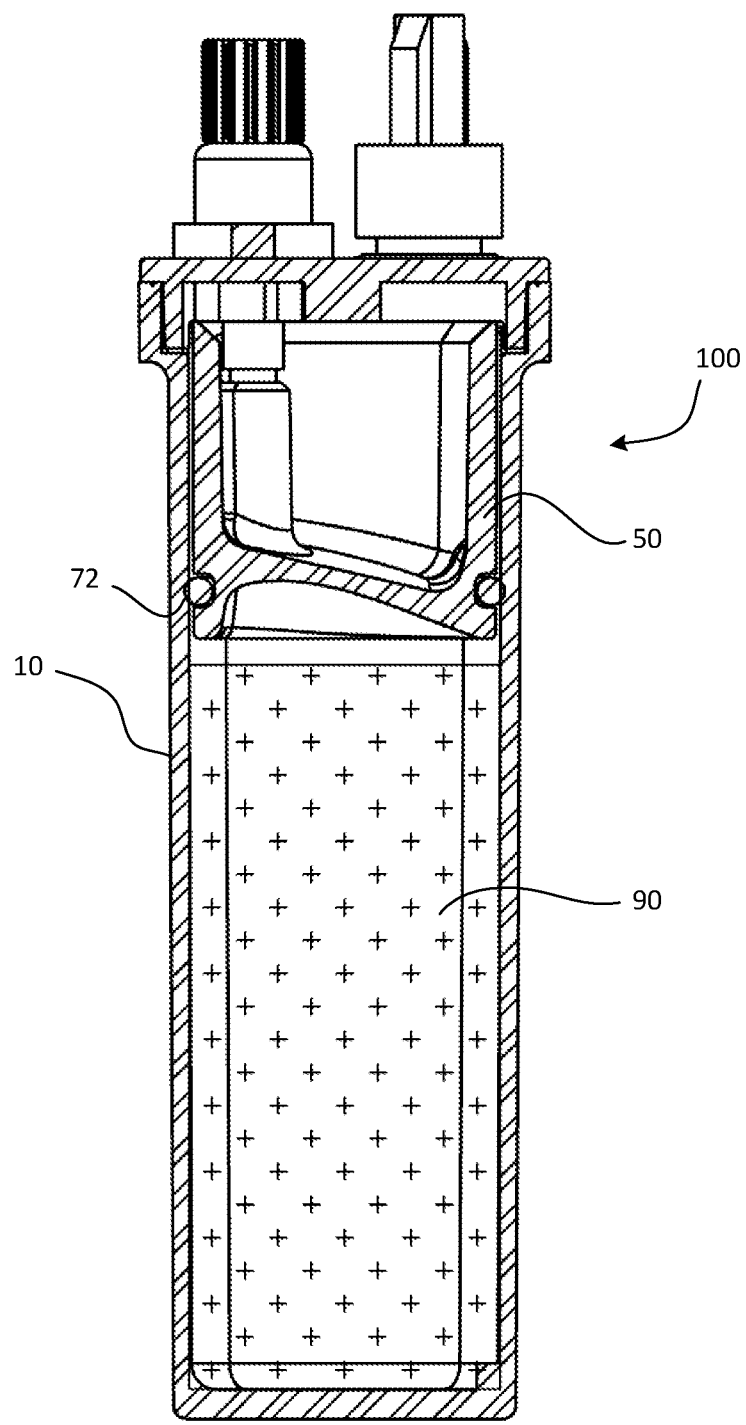
FIG. 5 is a front view of the device of FIG. 1A, with the insert in a proximal position and the tube filled with an unseparated blood sample.

Referring to FIGS. 5-9, the device 100 may be filled with 30-60 cc of whole blood 90 (anticoagulated) using a syringe connected to the first port 22 at the first end 12 of the device 100. The first port 22 may only be in fluid communication with the draw tube 62 for filling when the insert 50 is in an upward or proximal position within the tube 10, as shown in FIG. 5. In this position, the first port 22 may be in direct fluid communication with the draw tube 62, for example, via engagement of the boss 30 with the first opening 64 of the draw tube 62. Further, the first end 52 of the insert 50 may be in direct contact with the first end 12 of the tube, and/or in direct contact with the lid 20.

The device 100 is weighed and placed in the centrifuge, which may be any of a wide variety of commercially available centrifuges. A counterbalancing weight in the centrifuge may be added and/or adjusted to match the device weight. The device 100 is spun a first time, which may be for a duration of four minutes at 3,500 RPM, and removed from the centrifuge. The four-minute duration is merely exemplary; in other embodiments, a different duration may be used, and may range from 30 seconds to ten minutes. More specifically, the duration may range from one minute to eight minutes. Yet more specifically, the duration may range from two minutes to six minutes. Similarly, the 3,500 RPM speed is merely exemplary; in other embodiments, a different centrifugation speed may be used, and may range from 2,000 RPM to 5,000 RPM. More specifically, the centrifugation speed may range from 2,500 RPM to 4,500 RPM. Yet more specifically, the centrifugation speed may range from 3,000 RPM to 4,000 RPM.

Figure 6:
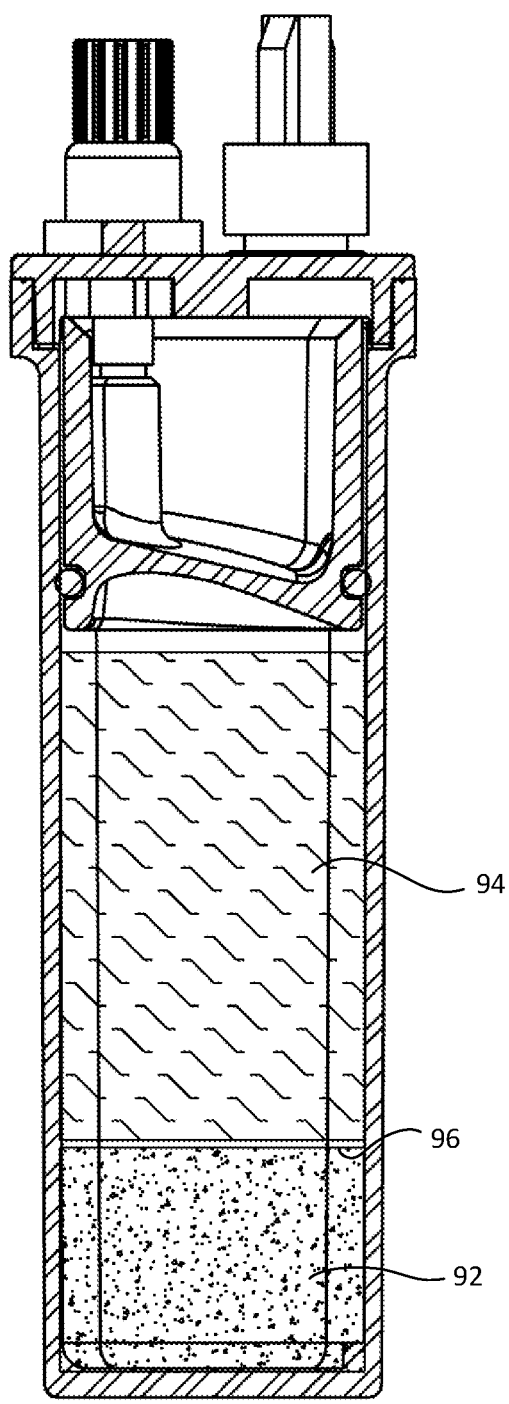
FIG. 6 is a front view of the device of FIG. 1A, with the insert in a proximal position and the tube filled with a blood sample which has been centrifuged to separate plasma and red blood cell layers of the sample.

As a result of the centrifugation, the blood may be separated with etythrocytes, which are red blood cells 92 (RBC) at the bottom and plasma 94 at the top. As shown in FIG. 6, an interface layer, or a buffy coat layer 96, is located at the interface between the red blood cells 92 and plasma 94 and contains a large portion of the platelets and white cells. The buffy coat layer 96 may contain white blood cells (leucocytes) and platelets. The insert 50 may not move relative to the tube 10 during centrifugation; rather, it may remain fixed in position relative to the tube 10.

Figure 7:
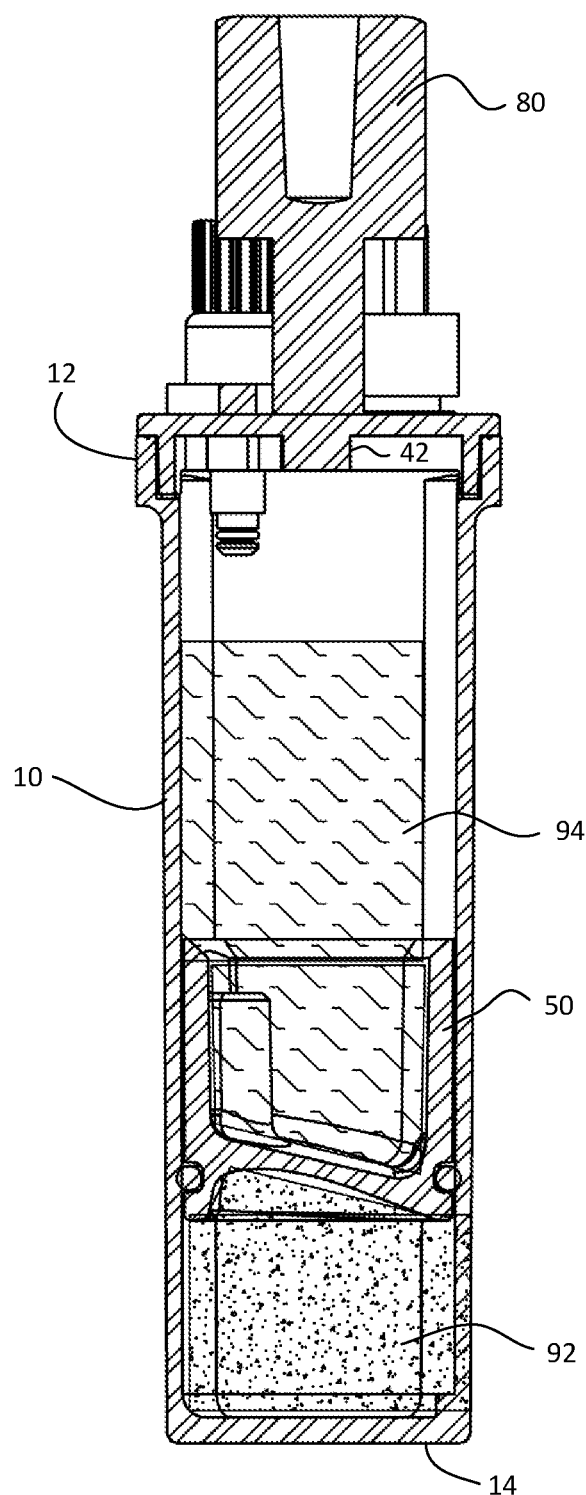
FIG. 7 is a front view of the device of FIG. 1A, wherein the insert has been moved toward the distal end of the tube and positioned at an interface between the plasma and red blood cell layers of the blood sample.

Referring to FIG. 7, following centrifugation, the lead screw 42 may be turned counter-clockwise to urge the insert 50 toward the second end 14 of the tube 10. A hand knob 80 may be provided for ease of turning the lead screw 42. The hand knob 80 may optionally be a separate piece from the device 100, and may have an interface (not shown) that enables the hand knob to be coupled to the head 44 of the lead screw 42.

As the insert 50 is lowered into the fluid (for example, into the plasma 94), a portion of the plasma 94 flows up through the draw tube 62. A user may be able to observe the plasma 94 as it flows upward though the draw tube 62 into the well 58 of the piston. When the buffy coat layer 96 has exited the top of the draw tube 62, a predetermined amount of red blood cells 92 can be allowed to exit the draw tube 62 as well, depending on the desired amount of red blood cells 92 in the final product. When the desired amount of the buffy coat layer 96 and any additional red blood cells 92 have exited through the draw tube 62, the user may cease turning the lead screw 42 to stop movement of the insert 50 relative to the tube 10.

The device 100 may then be placed back into the centrifuge. The centrifuge may then be activated to spin the device 100 for a second time. The counterbalancing weight may not need adjustment, since the total amount of fluid in the device 100 has not changed; i.e., fluid has not been added or removed. In one embodiment of the method in which a second spin is used, the second spin may be for five minutes at 3,800 RPM. As with the first spin, this duration and centrifugation speed are merely exemplary; the range of values for duration and centrifugation speed provided for the first spin is also applicable to the second spin.

Figure 8:
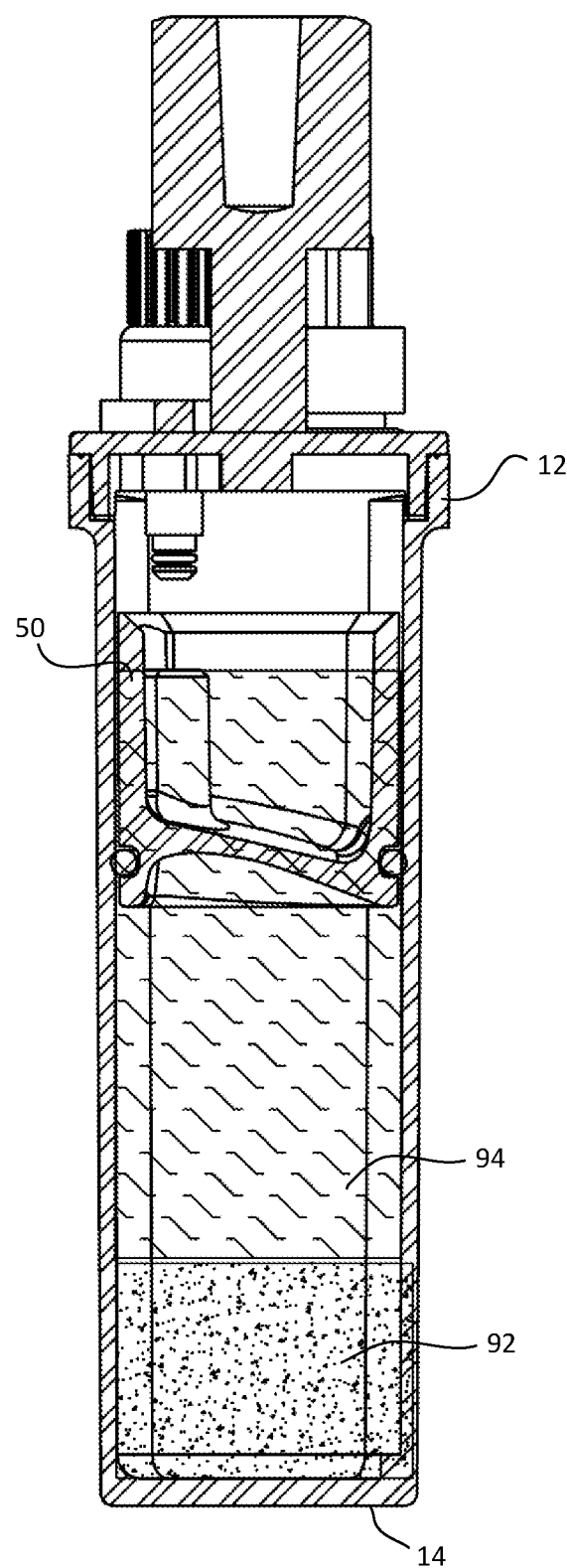
FIG. 8 is a front view of the device of FIG. 1A, wherein the insert has been moved toward the proximal end of the tube to capture buffy coat and platelet rich plasma in a chamber of the insert.
Figure 9:
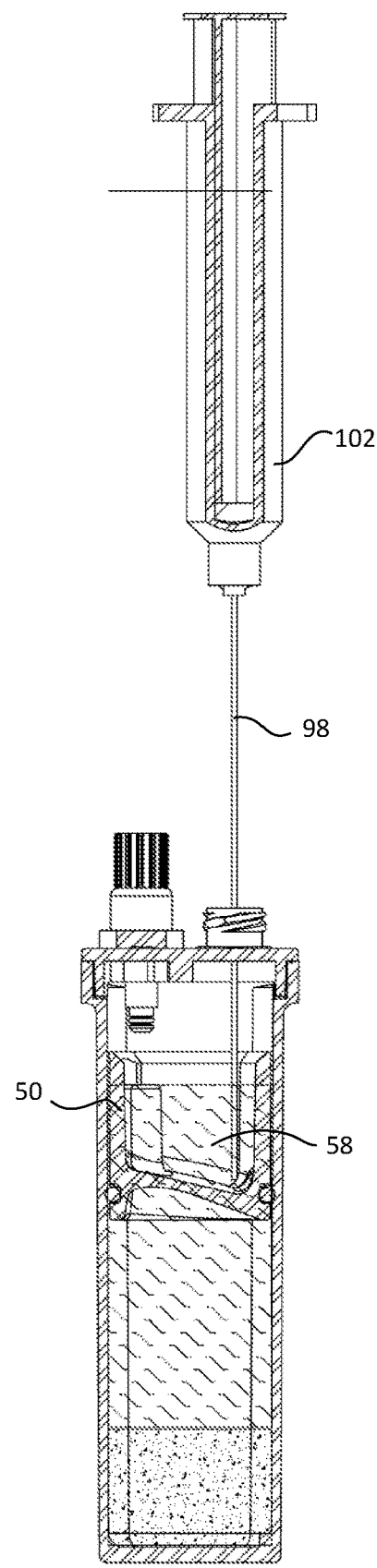
FIG. 9 is a front view of the device of FIG. 1A and a needle, wherein the needle is aspirating the buffy coat and platelet rich plasma from the chamber of the insert.

If a two-spin protocol is followed, following the second spin, the device 100 may be removed from the centrifuge. Referring to FIGS. 8 and 9, insert 50 may be raised toward the first end 12 by turning the lead screw 42 clockwise, for example, via the hand knob 80. This may allow the top portion of the plasma 94, which may be Platelet Poor Plasma (PPP), to drain back under the insert 50, leaving some of the buffy coat layer 96 and the remainder of the plasma 94 in the well 58 of the insert 50. In some embodiments, 7 cc of fluid may remain in the well 58, which may include some or all of the buffy coat layer 96 along with the remainder of the plasma 94, which may generally be Platelet Rich Plasma (PRP). The insert 50 may be raised until the level of PRP in the well 58 is below the first opening 64 of the draw tube 62; additionally or alternatively, the insert 50 may be raised until an air gap can be seen under the insert 50, between the insert 50 and the column of fluid.

A spinal needle 98 or other aspiration device may then be inserted through the second port 24 on the lid 20 of the device 100, and the 7 cc of fluid in the well 58 may be aspirated into a syringe 102 or other container. The fluid may be forced through the syringe 102 and back into the well 58 of the insert 50 to enhance mixing; this step may be repeated several times. In one embodiment, this step is repeated three times. In other embodiments, it may be repeated more or fewer than three times. After the final aspiration, the product in the syringe 102 may be well-mixed and ready for clinical application.

If a three-spin protocol is followed, after the second centrifuge spin, the device 100 may be removed from the centrifuge, and the lead screw 42 may again be turned counter-clockwise to urge the insert 50 to move further toward the second end 14 of the tube 10. The user may be able to observe the fluid as it flows upward though the draw tube 62 into the well 58 of the insert 50. When the buffy coat layer 96 has exited the top of the draw tube 62, a predetermined amount of the red blood cells 92 can be allowed to exit the draw tube 62 as well, depending on the desired amount of red blood cells 92 in the final product. When the desired amount of the buffy coat layer 96 and any additional red blood cells 92 have exited through the draw tube 62, the user may cease turning the lead screw 42 to stop movement of the insert 50 relative to the tube 10.

The device 100 may be placed back into the centrifuge and spun for a third time. Again, the counterbalancing weight may not need adjustment, since no fluid has been removed from the device 100. The third spin may be for 1.5 minutes at 3800 rpm. As with the first and second spins, this duration and centrifugation speed are merely exemplary; the range of values for centrifugation speed provided for the first spin is also applicable to the second spin. Different durations may be used, and may range from 30 seconds to five minutes. More specifically, the duration may range from one minute to three minutes. Yet more specifically, the duration may range from one-and-a-quarter minutes to two minutes.

In some embodiments, the durations and/or centrifugation speeds of the first spin and/or the second spin may be modified for the three-spin protocol. For example, the first spin and the second spin may each be carried out at 3500 RPM for two minutes. In such a case, the third spin may be performed at 3800 RPM for five minutes, like the second spin of the two-spin protocol. These durations and centrifugation speeds are merely exemplary; alternative durations and/or centrifugation speeds may be used, as set forth in the preceding descriptions of the first, second, and third spins.

Following the third spin, the device 100 may be removed from the centrifuge. The insert 50 may be raised toward the first end 12 by turning the lead screw 42 clockwise. The insert 50 may be raised until the level of PRP in the well 58 of the insert 50 is below the first opening 64 of the draw tube 62; additionally or alternatively, the insert 50 may be raised until an air gap can be seen under the insert 50, between the insert 50 and the column of fluid. This may allow the top portion of the plasma 94, which may be Platelet Poor Plasma (PPP), to drain back under the insert 50, leaving about 7 cc of the buffy coat layer 96 and PRP in the well 58 of the insert 50. The spinal needle 98 or other aspiration device may then be inserted through the second port 24 on the lid 20 of the device 100, and the 7 cc of fluid may be aspirated into the syringe 102. The fluid may be forced through the syringe 102 and back into the well 58 of the insert 50 to enhance mixing; this step may be repeated several times. In one embodiment, this step is repeated three times; in other embodiments, it may be repeated more or fewer than three times. On the final aspiration, the product in the syringe 102 may be well-mixed and ready for clinical application.

In other embodiments of the method, more or less than 7 cc of fluid may be aspirated. Further, in other embodiments of the method, more than three centrifuge spins may be included to further concentrate the platelet rich plasma. The spin times and RPMs may vary, as described previously.

If desired, prior to first use, the device 100 may be calibrated to determine the positions to which the insert 50 may be moved within the tube 10 to enable aspiration of the desired quantity of fluid (for example, 7 cc as set forth above). Such calibration may be done, for example, by moving the insert 50 toward the second end 14 and back toward the first end 12 of the tube, as outlined above, with another fluid such as water. The stop locations of the insert 50 may be noted, relative to the indicator marks 17 on the tube 10, at which the desired quantity of fluid is obtained from the well 58 of the insert 50.

The two-spin protocol and the three-spin protocol may both be carried out through use of the device 100. The three-spin protocol may have the potential to recover more platelets, thus providing a higher platelet concentration in the final product. The two-spin protocol may be faster while still providing adequate platelet concentration for many applications.

The devices and methods described herein may be used with other fluids, for example bone marrow aspirate, cell suspensions, and/or any other fluid that is separable into fractions. Although the method refers to a blood separation, it will be understood that the present invention may be used to separate and concentrate any appropriate fluid.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A method for separating a biological liquid sample and retrieving a separated liquid therefrom, the method comprising:
    depositing the biological liquid sample into an apparatus comprising:
        a tube having a proximal end, a distal end, and a chamber between the proximal end and the distal end;
        a lid that encloses the proximal end, the lid comprising a first port and a second port displaced from the first port; and
        an insert positioned in the chamber, the insert having a first end, a second end, a well between the first end and the second end, and a draw tube in fluid communication with the second end and the well;
    wherein depositing the biological liquid sample into the apparatus comprises depositing the biological liquid sample through the first port, through the draw tube and into the chamber distal to the insert;
    centrifuging the tube so that separated liquid collects in the chamber, distal to the second end;
    moving the insert distally toward the separated liquid to allow the separated liquid to flow proximally from the chamber through the draw tube and collect in the well; and
    retrieving the separated liquid from the well by:
        moving the insert proximally toward the proximal end; and
        aspirating the separated liquid from the well through the second port.

2. The method of claim 1, wherein moving the insert distally comprises actuating a positioning mechanism, connected to the tube and the insert, that defines a longitudinal axis, wherein moving the insert comprises translating the insert relative to the tube and the positioning mechanism along the longitudinal axis.

3. The method of claim 2, wherein the positioning mechanism is a lead screw extending from the proximal end into the chamber toward the distal end, wherein actuating the positioning mechanism comprises turning the lead screw.

4. The method of claim 2, wherein moving the insert distally comprises:
    translating the insert from a first position at the proximal end toward the distal end; and
    stopping the insert at a selected position displaced distally from the proximal end.

5. The method of claim 1, further comprising, after moving the insert distally and prior to aspirating the separated liquid from the well, centrifuging the biological liquid sample a second time.

6. The method of claim 5, further comprising:
after centrifuging the biological liquid sample the second time, moving the insert a second time distally toward the separated liquid to allow the separated liquid to flow proximally from the chamber through the draw tube and collect in the well; and
after moving the insert the second time and prior to aspirating the separated liquid from the well, centrifuging the biological liquid sample a third time.

7. The method of claim 1, wherein:
upon centrifugation of the tube the biological liquid sample separates into a first layer, a second layer, and an interface layer between the first and second layers; and
retrieving the separated liquid comprises retrieving the interface layer from the well.

8. The method of claim 1, wherein the insert remains stationary relative to the tube during centrifugation.

9. A method for separating a biological liquid sample and retrieving a separated liquid therefrom, the method comprising:
depositing the biological liquid sample into an apparatus comprising:
a tube having a proximal end, a distal end, and a chamber between the proximal end and the distal end; and
an insert positioned in the chamber, the insert having a first end, a second end, a well between the first end and the second end, and a draw tube in fluid communication with the second end and the well;
wherein depositing the biological liquid sample into the apparatus comprises depositing the biological liquid sample into the chamber, distal to the second end;
centrifuging the tube so that separated liquid collects in the chamber, distal to the second end;
moving the insert distally toward the separated liquid to allow the separated liquid to flow proximally from the chamber through the draw tube and collect in the well;
after moving the insert, centrifuging the biological liquid sample a second time; and
after centrifuging the biological liquid sample the second time, retrieving the separated liquid from the well.

10. The method of claim 9, wherein:
moving the insert distally comprises actuating a positioning mechanism, connected to the tube and the insert, that defines a longitudinal axis, wherein moving the insert comprises translating the insert relative to the tube and the positioning mechanism along the longitudinal axis; and
the insert remains stationary relative to the tube during centrifugation.

11. The method of claim 10, wherein the positioning mechanism is a lead screw extending from the proximal end into the chamber toward the distal end, wherein actuating the positioning mechanism comprises turning the lead screw.

12. The method of claim 10, wherein moving the insert distally comprises:
translating the insert from a first position at the proximal end toward the distal end; and
stopping the insert at a selected position displaced distally from the proximal end.

13. The method of claim 9, further comprising:
after centrifuging the biological liquid sample the second time, moving the insert a second time distally toward the separated liquid to allow the separated liquid to flow proximally from the chamber through the draw tube and collect in the well; and
after moving the insert the second time and prior to aspirating the separated liquid from the well, centrifuging the biological liquid sample a third time.

14. The method of claim 9, wherein:
upon centrifugation of the tube the biological liquid sample separates into a first layer, a second layer, and an interface layer between the first and second layers; and
retrieving the separated liquid comprises retrieving the interface layer from the well.

15. A method for separating a biological liquid sample and retrieving a separated liquid therefrom, the method comprising:
depositing the biological liquid sample into an apparatus comprising:
a tube having a proximal end, a distal end, and a chamber between the proximal end and the distal end; and
an insert positioned in the chamber, the insert having a first end, a second end, a well between the first end and the second end, and a draw tube in fluid communication with the second end and the well;
wherein depositing the biological liquid sample into the apparatus comprises depositing the biological liquid sample into the chamber, distal to the second end;
centrifuging the tube so that separated liquid collects in the chamber, distal to the second end, the separated liquid comprising a first layer, a second layer, and an interface layer between the first and second layers;
moving the insert distally toward the separated liquid to allow the separated liquid to flow proximally from the chamber through the draw tube and collect in the well; and
retrieving the interface layer from the well.

16. The method of claim 15, wherein:
moving the insert distally comprises actuating a positioning mechanism, connected to the tube and the insert, that defines a longitudinal axis, wherein moving the insert comprises translating the insert relative to the tube and the positioning mechanism along the longitudinal axis; and
the insert remains stationary relative to the tube during centrifugation.

17. The method of claim 15, wherein the positioning mechanism is a lead screw extending from the proximal end into the chamber toward the distal end, wherein actuating the positioning mechanism comprises turning the lead screw.

18. The method of claim 15, wherein moving the insert distally comprises:
translating the insert from a first position at the proximal end toward the distal end; and
stopping the insert at a selected position displaced distally from the proximal end.

19. The method of claim 15, further comprising, after moving the insert and prior to aspirating the separated liquid from the well, centrifuging the biological liquid sample a second time.

20. The method of claim 19, further comprising:
after centrifuging the biological liquid sample the second time, moving the insert a second time distally toward the separated liquid to allow the separated liquid to flow proximally from the chamber through the draw tube and collect in the well; and
after moving the insert the second time and prior to aspirating the separated liquid from the well, centrifuging the biological liquid sample a third time.

* * * * *